United States Patent
Olek et al.

(10) Patent No.: US 9,556,484 B2
(45) Date of Patent: Jan. 31, 2017

(54) EPIGENETIC MARKER FOR THE IDENTIFICATION OF IL17 POSITIVE T CELLS IN COMPLEX SAMPLES

(71) Applicant: Epiontis GmbH, Berlin (DE)

(72) Inventors: Sven Olek, Berlin (DE); Udo Baron, Berlin (DE)

(73) Assignee: EPIONTIS GMBH, Berlin (DE)

( * ) Notice: Subject to any disclaimer, the term of this patent is extended or adjusted under 35 U.S.C. 154(b) by 216 days.

(21) Appl. No.: 14/350,234

(22) PCT Filed: Oct. 18, 2012

(86) PCT No.: PCT/EP2012/070676
§ 371 (c)(1),
(2) Date: Apr. 7, 2014

(87) PCT Pub. No.: WO2013/057202
PCT Pub. Date: Apr. 25, 2013

(65) Prior Publication Data
US 2014/0227703 A1    Aug. 14, 2014

(30) Foreign Application Priority Data
Oct. 18, 2011   (GB) .................................. 1117904.1

(51) Int. Cl.
*C07H 21/02*   (2006.01)
*C07H 21/04*   (2006.01)
*C12Q 1/68*    (2006.01)

(52) U.S. Cl.
CPC ....... *C12Q 1/6881* (2013.01); *C12Q 2600/154* (2013.01)

(58) Field of Classification Search
None
See application file for complete search history.

(56) References Cited

PUBLICATIONS

Janson, Peter C.J. et al., "Profiling of CD4+ T Cells with Epigenetic Immune Lineage Analysis," *The Journal of Immunology*, 2011, vol. 186, p. 92-102.

Lexberg, Maria Helen. "Stability and plasticity of IL-17 expression in $T_H17$ cells", Jan. 2010, XP055047853, Retrieved from the Internet: http://opus.kobv.de/tuberlin/volltexte/2010/2790/pdf/lexberg_maria.pdf.

Liu, Jing et al., "T Regulatory Cells in Cord Blood—FOXP3 Demethylation as Reliable Quantitative Marker," PLoS ONE, Oct. 2010, vol. 5, Issue 10, p. 1-7.

Singh, Narendra P. et al., "Activation of Aryl Hydrocarbon Receptor (AhR) Leads to Reciprocal Epigenetic Regulation of FoxP3 and IL-17 Expression and Amelioration of Experimental Colitis," *PLoS ONE*, Aug. 2011, vol. 6, Issue 8, p. 1-13.

*Primary Examiner* — Jehanne Sitton
(74) *Attorney, Agent, or Firm* — Saliwanchik, Lloyd & Eisenschenk (57) ABSTRACT

The present invention relates to a method, in particular an in vitro method for identifying IL-17 expressing T cells in a blood and/or tissue sample derived from a mammal, comprising analysing the methylation status of at least one CpG position in the gene IL-17A, wherein a demethylation of said at least one CpG position in said sample when compared to an analogous position in a non IL-17 blood cell is indicative for a IL-17 positive CD4 positive T cell. The analyses according to the invention can identify IL-17 positive T cells and distinguish them from all other cells in complex samples, such as, for example, other blood cells. The present invention furthermore provides an improved method for quantifying IL-17 positive T cells in complex samples based on a comparison of the IL-17A methylation with a methylation of at least one marker selected from the group of CD3, FOXP3, and/or GAPDH. The method can be performed without a step of purifying and/or enriching cells, preferably in whole blood and/or non-trypsinized tissue.

17 Claims, 4 Drawing Sheets

5′AAGAATGAAAAGAGGACATGGTCTTTAGGAACATGAATTTCTGCCCTTCCCATTTTCCTTC
AGAAGGAGAGATTCTTCTATGACCTCATTGGGGCGGAAATTTTAACCAAAATGGTGTCACC
CCTGAACCCACTGCGACACGCCACGTAAGTGACCACAGAAGGAGAAAAGCCCTATAAAAAGA
GAGACGATAGCGCTACATTTTGTCCATCTCATAGCAGGCACAAACTCATCCATCCCCAGTTG
ATTGGAAGAAACAACGATGACTCCTGGGAAGACCTCATTGGTGGTGAGTCCTGCACTAACGT
GCGATGCTCTTGCTGATTTGGACCAGATAGTATTTCTGGACCGTGGGCATGAAACGCTGGGT
TCTGACTATGGAGATCCAGGAA3′

B

5′TCTTCTATAACCTCATTAAAAACAAAAATTTTAACCAAAATAATATCACCCCTAAACCCAC
TACAACACACCACATAAATAACCACAAAAAAAAAAAAACCCTATAAAAAAAAAACAATAAC
ACTACATTTTATCCATCTC3′

C

5′AACCCACTACAACACACCACATAAATAACCACAAAAAAAAAAAAACCCTATAAA**AAAAAAA
ACAATAACACTACATTTTA**TCCATCTCATAACAAACACAAACTCATCCATCCCCAATTAATT
AAAAAAAACAACAATAACTCCTAAAAAAACCTCATTAATAATAAATCCTACACTAACATACA
ATACTCTTACTAATTTAAACCA3′

EPIGENETIC MARKER FOR THE IDENTIFICATION OF IL17 POSITIVE T CELLS IN COMPLEX SAMPLES

CROSS REFERENCE TO A RELATED APPLICATION

This application is a National Stage Application of International Application Number PCT/EP2012/070676, filed Oct. 18, 2012; which claims priority to Great Britain Application No. 1117904.1, filed Oct. 18, 2011; which are incorporated herein by reference in their entirety.

The Sequence Listing for this application is labeled "SEQLIST-07APR14-ST25.txt", which was created on Apr. 7, 2014, and is 7 KB. The entire content is incorporated herein by reference in its entirety.

The present invention relates to a method, in particular an in vitro method for identifying IL-17 expressing T cells in a blood and/or tissue sample derived from a mammal, comprising analyzing the methylation status of at least one CpG position in the gene IL-17A, wherein a demethylation of said at least one CpG position in said sample when compared to an analogous position in a IL-17 negative blood cell is indicative for a IL-17 positive CD4 positive T cell. The analyses according to the invention can identify IL17 positive T cells and distinguish them from all other cells in complex samples, such as, for example, other blood cells. The present invention furthermore provides an improved method for quantifying IL17 positive T cells in complex samples based on a comparison of the IL17A methylation with a methylation of at least one marker selected from the group of CD3, FOXP3, and/or GAPDH. The method can be performed without a step of purifying and/or enriching cells, preferably in whole blood and/or non-trypsinized tissue.

BACKGROUND OF THE INVENTION

T helper 17 cells (Th17) are a subset of T helper cells producing interleukin 17 (IL-17) discovered in 2007. They are considered developmentally distinct from Th1 and Th2 cells and excessive amounts of the cell are thought to play a key role in autoimmune disease (Stockinger B, Veldhoen M (June 2007). "Differentiation and function of Th17 T cells". Current Opinion in Immunology 19 (3): 281-286) such as multiple sclerosis (which was previously thought to be caused by Th1 cells), but also psoriasis, autoimmune uveitis, juvenile diabetes, rheumatoid arthritis, and Crohn's disease.

Th17 cells primarily produce two main members of the IL-17 family, IL-17A and IL-17F, which are involved in the recruitment, activation and migration of neutrophils. These cells also secrete IL-21 and IL-22. Recently, Th17 polarized cells have been shown to mediate the regression of established tumors in mice (Martin-Orozco N, Muranski P, Chung Y et al. (November 2009). "T helper 17 cells promote cytotoxic T cell activation in tumor immunity". Immunity 31 (5): 787-798).

Even though almost all cells in an individual contain the exact same complement of DNA code, higher organisms must impose and maintain different patterns of gene expression in the various tissue types. Most gene regulation is transitory, depending on the current state of the cell and changes in external stimuli. Persistent regulation, on the other hand, is a primary role of epigenetics—heritable regulatory patterns that do not alter the basic genetic coding of the DNA.

As explained below, one form of epigenetic modification is the attachment of methyl groups to the base cytosine. Nevertheless, in addition to the "fifth base" 5-methylcytosine (mC), a sixth (5-hydroxymethylcytosine, hmC), seventh (5-formylcytosine, fC) and eighth (5-carboxycytosine, cC) can be found (Michael J. Booth et al. Quantitative Sequencing of 5-Methylcytosine and 5-Hydroxymethylcytosine at Single-Base Resolution Science 18 May 2012, Vol. 336 no. 6083 pp. 934-937). Both, 5-methylcytosine and 5-hydroxymethylcytosine are not bisulfite convertible.

DNA methylation is the archetypical form of epigenetic regulation; it serves as the stable memory for cells and performs a crucial role in maintaining the long-term identity of various cell types. The primary target of methylation is the two-nucleotide sequence Cytosine-Guanine (a 'CpG site'); within this context cytosine (C) can undergo a simple chemical modification to become formylated, methylated, hydroxymethylated, carboxylated. In the human genome, the CG sequence is much rarer than expected except in certain relatively dense clusters called 'CpG islands'. CpG islands are frequently associated with gene promoters, and it has been estimated that more than half of the human genes have CpG islands (Antequera and Bird, Proc Natl Acad Sci USA. 90:11995-9, 1993).

At this point, there is a very abrupt change from DNA methylation to Treg biology. Thus, one could include a bridging phrase such as: It has been shown that distinct cell types display a unique and characteristic DNA methylation pattern, i.e., an epigenetic fingerprint that can be exploited for cell type identification and quantification (DNA methylation analysis as a tool for cell typing. Baron U, Türbachova I, Hellwag A, Eckhardt F, Berlin K, Hoffmuller U, Gardina P, Olek S. Epigenetics. 2006 January-March; 1(1): 55-60. Epub 2006 Feb. 25.). Moreover, regulatory T cells, establishing tolerance for self-antigens but allowing immune responses against foes, were characterized to be exclusively demethylated in the FOXP3 gene, a master transcription factor pivotal for Treg differentiation and function (Epigenetic control of the foxp3 locus in regulatory T cells. Floess S, Freyer J, Siewert C, Baron U, Olek S, Polansky J, Schlawe K, Chang H D, Bopp T, Schmitt E, Klein-Hessling S, Serfling E, Hamann A, Huehn J. PLoS Biol. 2007 February; 5(2):e38.; DNA demethylation in the human FOXP3 locus discriminates regulatory T cells from activated FOXP3(+) conventional T cells. Baron U, Floess S, Wieczorek G, Baumann K, Grützkau A, Dong J, Thiel A, Boeld T J, Hoffmann P, Edinger M, Türbachova I, Hamann A, Olek S, Huehn J. Eur J Immunol. 2007 September; 37(9):2378-89.)

The adoptive transfer of in vitro expanded Treg is a promising treatment option for autoimmune as well as alloantigen-induced diseases. Yet, concerns about the phenotypic and functional stability of Tregs upon in vitro culture command both careful selection of the starting population and thorough characterization of the final cell product.

Recently, a high degree of developmental plasticity has been described for murine Treg and Th17 cells. Similarly, IL-17-producing FOXP3(+) cells have been detected among the CD45RA(-) memory-type subpopulation of human Tregs ex vivo. This prompted the investigation of the predisposition of human naïve and memory Tregs to develop into Th17 cells during polyclonal in vitro expansion. Stimulation-induced DNA demethylation of RORC, which encodes the lineage-defining transcription factor for Th17 cells, occurs selectively in CD45RA(-) memory-type Tregs, irrespective of their FOXP3 expression level. On the contrary, naïve CD45RA(+) Tregs retain stable CpG methylation across the RORC locus even upon prolonged ex vivo expansion and in consequence show only a marginal tendency to express RORC and develop into IL-17-producing cells (Schmidl C, Hansmann L, Andreesen R, Edinger M, Hoffmann P, Rehli M. Epigenetic reprogramming of the RORC locus during in vitro expansion is a distinctive feature of human memory but not naïve Treg. Eur J Immunol. 2011 May; 41(5):1491-8. Epub 2011 Apr. 12).

It is commonly thought that immune cell quantification is relatively easy and fully standardized, since the non-adherent, non-matrixed cells in peripheral blood can be marked with antibodies and flow-cytometrically quantified. Providing that cells are non-adherent, single cell suspensions, intact and cell-type specific surface antigens are available, flow cytometry is indeed a highly accurate cell quantification tool.

However, for many applications in research and medical routine, the named prerequisites for such precise measurements are not given:
1. Often, the material/samples measured are not derived from peripheral blood and thus the solubility and single cell suspension property is not met. This is for example true for all biopsy analyzes, such as performed in the pathological routine.
2. Even if the analyte is peripheral blood, the prerequisite of having intact cells is difficult to meet, since—in order to maintain their structural integrity ("intactness")—these cells must not be frozen or stored as EDTA-blood for more than 6 hours, before subfractions, such as granulocytes start disintegrating.
3. In contrast to the common perception, there are not highly specific (surface) antigens for all immune cell types and hence the identification of cell types is not as unambiguous as may be hoped.
3a. Since antigen expression is not a digital process, thresholds must be defined to decide, whether cells belong to the positive or negative fraction. For T cells, this problem is particular apparent:

Hence, for many applications the current methodological approaches for a quantitative determination of immune cells remain problematic, such as for routine testing in clinical applications, which usually requires some lag times, and hence robustness and stability of the analyte. As said, the flow cytometric methods used for measurement of cells in peripheral blood are not adequate for immune cells infiltrating other tissues, including solid tissues during tumor development or at/after inflammation. Hence, flow cytometric methods are not applied in these areas and the surrogate methods (mostly immune histochemistry) are at most semi-quantitative methods.

For the purpose of definition for the present application, epigenetic modifications in the DNA sequence is referred to by the terminology of DNA methylation (5-methylcytosine (mC), 5-hydroxymethylcytosine, (hmC), 5-formylcytosine, (fC) and/or 5-carboxycytosine (cC)). Both, at least, 5-methylcytosine and 5-hydroxymethylcytosine are not bisulfite convertible and cannot be distinguished via bisulfite conversion analysis.

In the scientific literature, the status of methylation is often displayed as either "hyper" (above, more than normal, (lat.: super)) or "hypo" (below, less than normal, (lat.: sub) methylation. In the view of the inventor, these terms are inappropriate, since they suggest variance from the "normal" status. For healthy cells however, there is no such thing as non-normal, since for one cell type it is normal that it is methylated whereas the other is unmethylated.

Both signatures are perfectly normal. For the inventor, gene regions are therefore either methylated or unmethylated (also and equivalent to unmethylated: demethylated). The potential decision as to whether a region in a cell type is aberrantly methylated (hypermethylated) or aberrantly demethylated (hypomethylated) may potentially play a role in certain diseases and decision may be made based on this. However, it is not an issue that is discussed or found in the technical process of measuring the methylation status in DNA. Despite this and owing to the general rules, whenever hypermethylation and hypomethylation is written it is thought to indicate the technical classification of demethylation and methylation.

The NCBI Reference Sequence: NC_000006.11 discloses chromosome 6, including the genomic region for human IL17A (Chromosome 6: position for the mRNA is 52,051, 185-52,055,436 on the forward strand).

The present inventors present a marker that can be used for the identification and quantification of IL17 positive T cells in an alternative quantitative, more efficient, robust and integral approach: the analysis of cell type-, or cell status-specific epigenetic (DNA methylation and or chromatin structure and or DNA chemical inertness) markers. In the clinical routine and the general cell biological practice, the identification of specific epigenetic markers will greatly facilitate the measurement of blood and immune cell types.

Janson et al. (in Janson P C, Linton L B, Bergman E A, Marits P, Eberhardson M, Piehl F, Malmström V, Winqvist O. Profiling of CD4+ T cells with epigenetic immune lineage analysis. J Immunol. 2011 Jan. 1;186(1):92-102. Epub 2010 Dec. 3. ) describe a method to pinpoint the location of isolated human CD4(+) T cells on any T cell effector axis based on specific CpG methylation of cytokine and transcription factor loci. They applied such a method on CD4(+) cells obtained from rheumatoid arthritis and multiple sclerosis patients and showed that synovial fluid infiltrating CD4(+) T cells are committed toward both Th1 and regulatory T cell phenotype, whereas the Th2 response is suppressed. Furthermore, they showed that the IL-17A gene is regulated by promoter methylation and that Th17 commitment is not a common feature in the inflamed joints of rheumatoid arthritis patients. They concluded that the method described in the publication thus would allow for accurate profiling of Th lineage commitment in ex vivo-isolated CD4(+) T cells.

The importance of methylation becomes particularly apparent in tumor cells. Here, the "normal" methylation patterns—that are essential for a healthy development of a cell—are lost, and the cells therefore can no longer be controlled, and become not only epigenetically aberrant. Although aberrant methylation is not the primary subject of the present invention, the apparent significance of a correct epigenetic regulation becomes apparent by the close association between cancer cells and wrong methylation. Form this, one can conclude on the importance of a correct methylation. For single genes, as was shown earlier with the FOXP3 (Baron et al, Eur J Immunol. 2007 Sep.; 37(9):2378-89; Wieczorek et al. Cancer Res. 2009 Jan. 15; 69(2):599-608) and CD3 locus (Sehouli et al. Epigenetics. 2011 Feb. 1; 6(2):236-46), the chemical/structural nature of the DNA at the given loci (such as the methylation status/imprint) coincides with the differentiation and the type of certain cells. This allows for an identification and quantification of the cell type of healthy cells based on their epigenetic fingerprint. Whether the highly inflammatory nature of Th17 cells is sufficient to cause or contribute to carcinogenesis is the subject of current debate (Wu S, Rhee K J, Albesiano E et al. (September 2009). "A human colonic commensal promotes colon tumorigenesis via activation of T helper type 17 T cell responses". Nature Medicine 15 (9): 1016-1022; Huang C, Fu Z X. Localization of IL-17+Foxp3+ T cells in esophageal cancer. Immunol Invest. 2011; 40(4):400-12. Epub 2011 Feb. 11.).

In view of the above, despite of some progresses in the art, it is an object of the present invention to provide an improved method based on accessibility to bisulfite conversion and/or DNA methylation analysis as a superior tool in order to more conveniently and reliably identify and quantify IL17 positive T cells in a given sample derived/obtained from for example animal/human blood or tissue. Measurement can advantageously be done independent of purification, storage and to quite some extend also to tissue quality.

In further view of the above, it is an object of the present invention to provide an improved method to identify not only actual IL-17 protein producing cells but also cells that are capable of producing IL-17 protein after stimulation by e.g. ionomycin and PMA (phorbol myristate acetate). Currently, common techniques of cell identification only detect cells that are currently producing the IL-17 protein (up to 0.1% of cells within whole blood). However, the proportion of cells identified by the present invention amounts to 0.1-2% encompassing cells that are capable to produce IL-17 (currently not producing IL-17), too. IL17 positive cells are cells such as Th17 cells.

In a first aspect thereof, the invention solves the above problem by providing a method for identifying IL-17 positive CD4 positive T cells (also designated herein as IL-17 expressing T cells) in a blood and/or tissue sample derived from a mammal, comprising analysing the methylation status of at least one CpG position in the gene IL-17A, wherein a demethylation of said at least one CpG position in said sample when compared to an analogous position in a non IL-17 blood cell is indicative for an IL-17 positive CD4 positive T cell, such as Th17 cells.

Preferably, said method is performed without a step of purifying and/or enriching cells, preferably in whole blood and/or non-trypsinized tissue, or any other biological sample potentially containing T cells. Most preferably, said sample is a sample for autologous cell transfer into a patient, that is, is a sample to be transplanted into a patient.

A further embodiment of the invention then comprises the inventive method, wherein said method further comprises the quantification of Th17 cells in complex tissues compared to either natural Tregs, overall T cells and/or the respective tissue, in particular blood or solid diseased tissue, or adjacent tissue irrespective of its origin. In another aspect, IL17A can be part of a "Panel" of genes/markers, such as, for example, CD3, FOXP3 and/or GAPDH, as measured in case of several cell types that are important for the immune status of the mammal.

A further embodiment of the invention then comprises the inventive method, wherein said at least one CpG position is present in the 5' region upstream from the transcription start, promoter region, the 5' or 3' untranslated regions, intron, and/or exon/intron border, or in the 3' region downstream of the transcriptional stop.

A yet further embodiment of the invention then comprises the inventive method, wherein said at least one CpG position is selected from the CpG positions located in the gene IL17A according to SEQ ID NO: 17, preferably of the IL17A amplicon 1909 according to SEQ ID NO: 1, preferably a target region according to SEQ ID No: 2 or 3, or an IL17A amplicon as amplified with a primer pair selected from the sequences according to SEQ ID NOs: 4 to 16, or 18 to 21, particularly as amplified with the primer pair according to SEQ ID NO 19 and 20.

For a particular CpG as analyzed, theoretically there are four states per cell: (both alleles methylated), (allele A methylated, allele B unmethylated), (allele A unmethylated, allele B methylated), and (both alleles unmethylated). This leads to three different results: 100% methylated, 50% methylated and 0% methylated. Thus, theoretically IL-17 positive T cells are 0% methylated, and non-IL-17 positive T cells are approximately 100% methylated. A similar situation is present for the assay analyzing the accessibility of the region as analyzed to bisulfite conversion, where IL-17 positive T cells are 0% accessible, and non-IL-17 positive T cells are approximately 100% accessible.

In practical measurements employing e.g. bisulfite sequencing, the complete, "pure" methylation patterns are rarely detected, since both slight technical deficits of the employed technologies and possibly minor biological variances blur the theoretically expected values. Therefore, methods of the invention are preferred, wherein said at least one CpG position in said region as analyzed is demethylated to more than 80%, preferably more than 90%, and most preferred more than 95%, when compared to an analogous position in a non-IL-17 positive T cell.

Furthermore, the present invention includes methods, where more than one CpG position in a region is analyzed, such as, for example, 1, 2, 3, 4, 5, 6, 7, 8, 9, or 10 positions (e.g. in the AMP 1909 region (SEQ ID No. 1) as above). Then, an overall methylation (or demethylation) of the region as analyzed can be determined, when compared to an analogous region in a non-IL-17 positive T cell. Therefore, also methods of the invention are preferred, wherein said region is demethylated (hypomethylated) to more than 70%, preferably more than 80%, or 90%, and most preferred more than 95% when compared to an analogous region (hyper or fully methylated) in a non-IL-17 positive T cell.

The person of skill will furthermore be able to select specific subsets of CpG positions in order to minimize the amount of sites to be analyzed, for example all sites as present on the amplicon according to SEQ ID No. 1, or any other selected sub-sequence in the IL-17 gene as analyzed, for example as described above of the 5' region upstream from the transcription start, promoter region, the 5' or 3' untranslated regions, intron, and/or exon/intron border, or in the 3' region downstream of the transcriptional stop, and/or the target regions according to SEQ ID No. 2 or 3, or an IL17 amplicon as amplified with a primer pair selected from the sequences according to SEQ ID NOs: 4 to 16, or 18 to 21, particularly as amplified with the primer pair according to SEQ ID NO. 19 and 20.

Yet another aspect relates to a method according to the present invention, wherein the analysis of the accessibility to bisulfite conversion and/or the methylation status comprises a method selected from methylation specific enzymatic digests, bisulphite sequencing, analysis selected from promoter methylation, CpG island methylation, MSP, HeavyMethyl, MethyLight, Ms-SNuPE, qPCR or other methods relying on the detection of genomic DNA, chemically or enzymatically modified DNA or amplified genomic or chemically or enzymatically modified DNA. Also preferred is an additional analysis of the marker CD4, CD3, FOXP3, and/or GAPDH.

Another embodiment of the invention relates to the above methods, wherein said identification comprises a distinction and, optionally, a further quantification, of said IL-17 positive T cells from all major peripheral blood cell types or non-blood cells, and then further comprises the step of concluding on the immune status of said mammal based on said IL-17 expressing T cells as identified. Hereby, in a sample of a mammal, including whole blood or various subfractions as well as tissues or isolated subfractions of tissues, IL-17 positive T cells can be identified and quantified due to their (unique) methylation pattern in the analyzed genes. Based on this they can also be quantitated, as the loss of methylation strictly correlates with IL-17 positive T cells. The quantification preferably comprises a quantification of the IL-17 cells in said sample based on a comparison of the IL-17 methylation with a methylation of at least one marker selected from the group of CD3, FOXP3, and/or GAPDH.

Herein, the "immune status" of a person shall mean the status of the immune system of a given person in a given situation, in any given tissue type at any given disease situation. For example, it may be important to determine the immune status in a (tumor) tissue biopsy of a person who suffers from a solid tumor. Also, it may be relevant to determine the immune status of a (presumably) healthy person in the peripheral blood in order to determine the persons health status, whereby both an increase or a decrease of the cells—as quantified by the given number of methylated and unmethylated copies of the analyzed genes, in particular IL-17—may be indicative for a disease, such as for example, the presence of a tumor at an unknown site of the body, or an autoimmune reaction or a chronic infection.

In particular, the inventors regard the herein described methods to be suitable for routine application, for example on a DNA-chip. Samples are selected from a fresh, fresh-frozen or fully prepared (such as formalin fixed paraffin embedded) sample, including mammalian body fluid, preferable human blood samples, (serum samples) or tumorous or non-tumorous solid tissue samples, organ or cell type blood sample. These samples should be mammalian, preferably mouse, rat, monkey, bovine, swine or human. Especially preferred is a mammal, most preferred a human, which suffers from or is likely to suffer from IL-17 mediated diseases and side effects of anti-IL-17 therapies, such as, for example, psoriatic diseases, psoriasis, psoriatic arthritis, rheumatic diseases as e.g. rheumatoid arthritis, multiple sclerosis, arteriosclerosis, ankylosing spondylitis, Crohn's disease, inflammatory bowel disease, inflammatory diseases, uveitis, hepatitis diseases, lupus, lung diseases (e.g. asthma), hyper IgE syndrome, anti-tumor immunity, renal injuries, infections (viral, bacterial, fungal, parasitic) endotoxic shock, and autoimmune diseases, viral or bacterial infections, transplant rejections, cancer including solid and non solid cancers, and/or allergy or any disease directly correlated to IL-17 expressing T cells. The present invention can also be used to monitor anti-IL-17 therapies in a patient and/or patient group.

WO2012/093254A1 (incorporated by reference) describes the use of lipocalin 2 (LCN2) as a biomarker for IL-17 mediated diseases and for monitoring the response of a patient to anti-IL-17 therapy, and IL-17 related diseases that are also relevant for the present invention, such as a disorder selected from the group consisting of arthritis, rheumatoid arthritis, psoriasis, psoriatic arthritis, systemic onset juvenile idiopathic arthritis (HA), systemic lupus erythematosus (SLE), multiple sclerosis, asthma, chronic obstructive airway disease, chronic obstructive pulmonary disease, atopic dermatitis, scleroderma, systemic sclerosis, lung fibrosis, Crohn's disease, ulcerative colitis and ankylosing spondylitis and other spondyloarthropathies.

Yet another aspect relates to a method according to the present invention, further comprising the step of concluding on the number and/or amount of said IL-17 positive T cells as identified in said sample based on said identification and quantification. As the demethylation of the IL-17A gene and the amplicon according to SEQ ID No. 1 or the target regions according to SEQ ID No. 2 or 3, or an IL17 amplicon as amplified with a primer pair selected from the sequences according to SEQ ID NOs: 4 to 16, or 18 to 21, particularly as amplified with the primer pair according to SEQ ID NO. 19 and 20 are so strictly linked to the IL-17 expressing T cells, in the most convenient embodiment of said method, the number and/or amount of said IL-17 expressing T cells can be correlated directly with the results of the demethylation analysis, if normalized for the copy number in the assay and/or the gender of the subject. In other alternatives, additional control experiments (e.g. demethylated GAPDH analysis in parallel) may be applied (see also above).

In a further aspect the inventive method is useful for monitoring the level of IL-17 positive T cells in a mammal, comprising a method according to the invention, and comparing the amount of IL-17 positive T cells as identified with an earlier sample taken from the same mammal, and/or with a control sample.

Yet another aspect relates to a method according to the present invention, further comprising the step of concluding on the immune status of said mammal based on the number and/or amount of said IL17 expressing T cells as identified in said sample as described herein above.

Yet another aspect relates to a method according to the present invention, wherein said mammal suffers from or is likely to suffer from IL-17 mediated diseases and side effects of anti-IL-17 therapies, such as, for example, psoriatic diseases, psoriasis, psoriatic arthritis, rheumatic diseases as e.g. rheumatoid arthritis, multiple sclerosis, arteriosclerosis, ankylosing spondylitis, Crohn's disease, inflammatory bowel disease, inflammatory diseases, uveitis, hepatitis diseases, lupus, lung diseases (e.g. asthma), hyper IgE syndrome, anti-tumor immunity, renal injuries, infections (viral, bacterial, fungal, parasitic) endotoxic shock, and autoimmune diseases, viral or bacterial infections, transplant rejections, cancer including solid and non solid cancers, and/or allergy or any disease directly correlated to IL-17 expressing T cells.

In another aspect of the present invention, the method is also useful for measuring and/or monitoring the amount of said IL-17 expressing T cells in response to chemical and/or biological substances that are provided to said mammal.

In yet another aspect, the invention provides an amplicon according to SEQ ID NO: 1 or a target region thereof, preferably according to SEQ ID NOs. 2 or 3. The amplicon can be used as a tool in the methods according to the present invention.

The invention also provides a kit for identifying, quantifying, and/or monitoring IL-17 expressing T cells in a mammal based on the analysis of the methylation status of CpG positions in the gene IL-17, comprising materials for performing a method according to the invention as described hereinabove.

Such an inventive kit preferably comprises, but is not limited to, a) a bisulfite reagent, and b) materials for the methylation analysis of CpG positions selected from the CpG positions of the gene IL-17A according to SEQ ID NO: 17, preferably of the IL17 amplicon 1909 according to SEQ ID NO: 1, or an IL17 amplicon as amplified with a primer pair selected from the sequences according to SEQ ID NOs: 4 to 16, preferably a target region according to SEQ ID No: 2 or 3.

The present invention solves the above problem that the detection of IL-17 expressing T cells and their distinction from one another, is problematic in essentially all applications in the R&D and in particular in all clinical (routine) applications by providing a method for identifying IL-17 expressing T cells of a mammal, comprising analyzing the methylation status of at least one CpG position in one or various, for example regulatory, potentially differentially methylated regions of the gene for IL-17, wherein a demethylation, and/or accessibility to bisulfite conversion is highly specific or indicative for IL-17 expressing T cells.

In another preferred embodiment of the present invention, the inventors furthermore present a novel and more specific way in order to monitor IL-17 expressing T cells in all human body fluids, including human whole blood samples, or in any given (solid) tissue, organ or cell type.

The inventive concept is generally based on a specific demethylation and/or accessibility to bisulfite and other chemical base specific conversion of DNA of the genetic IL-17 region in IL-17 expressing T cells. Using a simple and precise quantitative PCR method, as a signal amplification method (e.g. a precise quantitative PCR method or other method allowing for the determination of copies of the nucleic acid molecules), the inventors show that the IL-17A region demethylation and/or accessibility to bisulfite conversion represents surrogate markers for IL-17 expressing T cell counts in blood or tissues. The present inventors have thus identified particular and new regions within the IL-17 gene that are functionally involved in, or reliably associated with, the existence of IL-17 expressing T cells.

The main aspect of the present invention is the distinction between and among functionally different fractions of T cells, namely the IL-17 expressing T cell fraction on one hand and other human/animal cell types on the other hand.

The inventors could demonstrate that in all IL-17 expressing T cells the CpG motifs are almost completely demethylated (i.e. to more than 70%, preferably 80%, preferably, more than 90% and most preferred more than 95%, see above), whereas the same motifs are completely methylated in all non-IL-17 expressing T cells. Determination of the methylation status of the IL-17 loci is therefore a valuable tool to identify IL-17 expressing T cells, such as will be required/or at least of some value for measuring IL-17 expressing T cells in autoimmune diseases, (viral) infections, transplant rejections, cancer, infections, and/or allergy. The assay allows measurement of IL-17 expressing T cells in "complex" biological samples (i.e. samples, such as tissue and/or blood) containing more than one type of cell, preferably more than one type of blood cell) without purification or any staining procedures. As a particularly preferred embodiment, the measurement of IL-17 expressing T cells by either of the markers described in here can be easily detected and quantified from within solid tissue samples of healthy or diseased nature, including tumorous or non-tumourous tissues. For such analysis it is possible to make the analysis either from fresh, fresh-frozen or any type of conserved (such as, for example, formalin fixed and/or paraffin-embedded) tissue. Another preferred embodiment is to determine the ratio between IL-17 expressing T cells on one hand and other T cell types on the other.

The inventors have shown that the potential to form IL-17 expressing T cell properties of mammalian immune cells coincide with epigenetic, i.e., DNA methylation based regulation in the genetic region of IL-17. DNA methylation is a biologically and chemically stable epigenetic modification, resulting in long-term gene expression changes. The inventors found demethylation and/or the accessibility of the genomic DNA to bisulfite conversion at the human IL-17 locus to be restricted to IL-17 expressing T cells when tested against all major peripheral blood cell types and a selection of different non-blood cell types/lines. These data indicated that epigenetic modifications in the IL-17A locus serve as valuable marker for the identification of cells with the phenotype of IL-17 expressing T cells, regardless of the expression of any genes.

It is well established in the art that often additional and important gene regulatory elements that are subject to gene regulation by methylation are located upstream and downstream of an open reading frame of a given gene—e.g. enhancer regions which are binding sites for indispensable transcriptional regulators. Thus, as a preferred embodiment of the present invention, an analysis of this elements is included in the methods of the present invention, which may be located within 10000 bases upstream of the transcriptional start site of IL-17A, preferably 9000 bases, 8000 bases, 7000 bases, 6000 bases, 5000 bases, 4000 bases, 3000 bases or 2000 bases upstream of IL-17A, even more preferred is a region 1000 bases upstream of the transcriptional start of IL-17A and most preferable in the first 500 bases upstream of the transcriptional start site of IL-17A. It is, however, particularly preferred that the sites as analyzed in the present invention are located within the gene promoter of IL-17A.

In another embodiment, the method according to the present invention is preferred, wherein said analysis of the methylation status comprises amplification with at least one primer of the primer pairs useful to amplify the amplicon according to SEQ ID NO: 1 or the target regions according to SEQ ID NOs 2 or 3.

Preferably, the amplification involves a polymerase enzyme, a PCR or chemical amplification reaction, or other amplification methods as known to the person of skill as described below, e.g. in the context of MSP, HeavyMethyl, Scorpion, MS-SNUPE, MethylLight, sequencing or methyl specific restriction assays. With the amplification, the amplicon of the IL-17A gene or any paralog or ortholog as described herein is produced that is a particularly preferred "tool" for performing the method(s) according to the present invention. Consequently, a primer pair for the amplification of the regions according to SEQ ID NO: 1 and SEQ ID NO: 17 and parts thereof and SEQ ID NOs 4 to 16 or 18 to 22, in particular of SEQ ID NO: 19 and SEQ ID NO: 20 constitutes a preferred embodiment of the present invention.

Furthermore, preferred is a method according to the invention, wherein above 5 mM of $MgCl_2$ are (can be) used in the amplification reaction, preferably up to 6.4 mM $MgCl_2$.

Furthermore, preferred is a method according to the invention, further comprising the step of analyzing the cellular markers CD3, CD4, FOXP3 and/or GAPDH. In order to analyze these additional markers, any known method to analyze expression can be used, such as methods using antibodies, and/or methylation analysis. The analysis of these markers preferably further improves the accuracy of the analysis, and might allow to identify sub-sets of cells. Thus, the method according to the present invention comprises an identification that is a distinction of said IL-17 expressing T cells from all major peripheral blood cell types or non-blood cells.

The method according to the present invention can be performed with any mammal having the above markers or orthologs or paralogs thereof, preferred is a method according to the present invention, wherein said mammal is a mouse, rat, pig or cow, monkey or human, preferably a human.

The method(s) according to the present invention can be performed in vitro and/or in vivo. In general, all biological samples can be used, as long as they contain suitable cells or suitable DNA of cells of interest. Preferred is a method wherein said sample is selected from a fresh, fresh-frozen or fully prepared sample including mammalian body fluid, preferable human whole blood samples, serum samples or a tumorous or non-tumorous solid tissue, organ or cell type blood sample, a sample of blood lymphocytes or a fraction thereof.

Another preferred aspect of the present invention then relates to the use of the method according to the present invention as above in diagnostics and the use in monitoring diseases. Thereby, in an alternative embodiment, the invention is directed at a method according to the present invention which further comprises the step of concluding on the immune status of said mammal based on said IL-17 expressing T cells as identified and/or quantified. In said method according to the invention, a demethylation of at least one CpG position in the gene IL-17A is indicative for an IL-17 expressing T cell.

Another important aspect of the present invention then relates to a method according to the present invention for monitoring the level of IL-17 expressing T cells in a mammal, comprising a method according to the invention as above, and comparing the amount of IL-17 expressing T cells as identified with an earlier sample taken from the same mammal, and/or with a control sample. Preferably, said method is performed on a sample from a mammal suffering from or is likely to suffer from autoimmune IL-17 mediated diseases and side effects of anti-IL-17 therapies, such as, for example, psoriatic diseases, psoriasis, psoriatic arthritis, rheumatic diseases as e.g. rheumatoid arthritis, multiple sclerosis, arteriosclerosis, ankylosing spondylitis, Crohn's disease, inflammatory bowel disease, inflammatory diseases, uveitis, hepatitis diseases, lupus, lung diseases (e.g. asthma), hyper IgE syndrome, anti-tumor immunity, renal injuries, infections (viral, bacterial, fungal, parasitic) endotoxic shock, and autoimmune diseases, viral or bacterial infections, transplant rejections, cancer including solid and non solid cancers, and/or allergy or any disease directly correlated to IL-17 expressing T cells.

Further preferred, said method according to the invention then further comprises measuring and/or monitoring the amount of IL-17 expressing T cells in response to chemical and/or biological substances that are provided to said mammal. That is, changes in the amount or ratio of IL-17 expressing T cells that are caused by, for example, the treatment of a disease (e.g. as described herein), and the success and/or progress of said treatment in terms of an effect on the IL-17 expressing T cells can be followed using this method. A follow-up of the methylation pattern based on the markers herein will point to changes in the cells that are due to a response to said chemical and/or biological substances, in some cases even before a phenotypic change can be observed.

In yet another aspect of the present invention, the present invention provides a method for identifying chemical and/or biological substances that selectively modulate IL-17 expressing T cells expressing the markers as described herein, comprising contacting one or more of said chemical and/or biological substance with potentially IL-17 expressing T cells, and detecting, whether said chemical and/or biological substance modulates the methylation of the CpG positions as analyzed, and/or whether said one or more of said chemical and/or biological substance selectively modulates the amount and/or ratio of marker-expressing IL-17 expressing T cells. Particularly preferred is a modulation of said IL-17 expressing T cells that increases the amount and/or ratio of said IL-17 expressing T cells.

The method can be performed in vitro and/or in a suitable animal. In this aspect, the present invention provides a method, sometimes called a "screening-method", that seeks to identify chemical and/or biological substances modulating expression of the markers as above that can be used as starting points for the development of IL-17 expressing T cell-specific medication and respective pharmaceutical compositions. The present method is based on the fact that it is well accepted that the marker genes as identified herein must play a central role for the development of IL-17 expressing T cells. Therefore, factors stimulating marker expression are interesting for the treatment of patients. Such factors, which lead to a stable modification, preferably induction, of the development/ratio/amount of IL-17 expressing T cells, can be detected with the method described in this invention.

Chemical and/or biological substances that are suitable as screening compounds are known to the person of skill and, for example, include small molecules, peptides and proteins, and antibodies or fragments thereof. Furthermore, the screening can be done using a commercially compound library, optimally together with suitable automation, such as a robot. In one preferred embodiment of the method for identifying chemical and/or biological substances, said substance provides a demethylation of the CpG positions as analyzed to at least 80%, preferably 90%, and more preferably 95%.

Another important aspect of the present invention then relates to a method according to the present invention, which further comprises the step of providing a treatment for a patient suffering from or being likely to suffer from IL-17 mediated diseases and side effects of anti-IL-17 therapies, such as, for example, psoriatic diseases, psoriasis, psoriatic arthritis, rheumatic diseases as e.g. rheumatoid arthritis, multiple sclerosis, arteriosclerosis, ankylosing spondylitis, Crohn's disease, inflammatory bowel disease, inflammatory diseases, uveitis, hepatitis diseases, lupus, lung diseases (e.g. asthma), hyper IgE syndrome, anti-tumor immunity, renal injuries, infections (viral, bacterial, fungal, parasitic) endotoxic shock, and autoimmune diseases, viral or bacterial infections, transplant rejections, cancer including solid and non solid cancers, and/or allergy or any disease directly correlated to IL-17 expressing T cells, wherein said treatment modulates, and preferably increases the amount and/or proportion of IL-17 expressing T cells in said, preferably, autoimmune or cancer patient. Preferred is a method according to the present invention, wherein said treatment is selected from providing chemical and/or biological substances that selectively stimulate IL-17 expressing T cells in said patient, or a treatment that stimulates the expression of the marker genes as above or supports the biological activity of said marker genes in said IL-17 expressing T cells in said patient. Preferred examples of such treatments are demethylating agents that provide for a reduced methylation of said genes. Other preferred examples of such treatments are agents that provide for a reduced number of IL-17 expressing T cells in case of autoimmune diseases.

Yet another preferred aspect of the present invention relates to an improved method of treatment of diseases that are related to marker gene expression and/or demethylation, IL-17 mediated diseases and side effects of anti-IL-17 therapies, such as, for example, psoriatic diseases, psoriasis, psoriatic arthritis, rheumatic diseases as e.g. rheumatoid arthritis, multiple sclerosis, arteriosclerosis, ankylosing spondylitis, Crohn's disease, inflammatory bowel disease, inflammatory diseases, uveitis, hepatitis diseases, lupus, lung diseases (e.g. asthma), hyper IgE syndrome, anti-tumor immunity, renal injuries, infections (viral, bacterial, fungal, parasitic) endotoxic shock, and autoimmune diseases, viral or bacterial infections, transplant rejections, cancer including solid and non solid cancers, and/or allergy or any disease directly correlated to IL-17 expressing T cells, comprising a method as described herein above. The term "treatment" also includes a prevention of marker gene expression and/or demethylation related diseases.

In yet another aspect of the present invention, the present invention relates to the use of an amplicon according to the present invention or a kit according to the present invention for identifying, quantifying and/or monitoring IL-17 expressing T cells in a mammal.

The present invention will now be further described in more detail in the form of preferred embodiments thereof in the following examples, nevertheless, without being limited thereto. For the purposes of the present invention, all references as cited herein are incorporated by reference in their entireties.

The upper Figure illustrates the TpG-(demethyl-)specific IL17A qPCR-system according to the invention. Amplification profiles of the plasmid standards (50000-80 copies) are shown. A (linear) standard curve was derived from the profiles by depicting the CP-value as measured over the logarithm of the template concentration. Amplification profiles of the blood sample are depicted in light gray, and labeled with the arrow. Dark gray curve: "no template"-control (NTC).

The lower Figure illustrates the TpG-(demethyl-)specific GAPDH qPCR-system. Amplification profiles of the plasmid standards (50000-16 copies) are shown. A (linear) standard curve was derived from the profiles by depicting the CP-value as measured over the logarithm of the template concentration. Amplification profiles of the blood sample are depicted in light gray, and labeled with the (light gray) arrow. Dark gray curve: "no template"-control (NTC).

Figure 2:
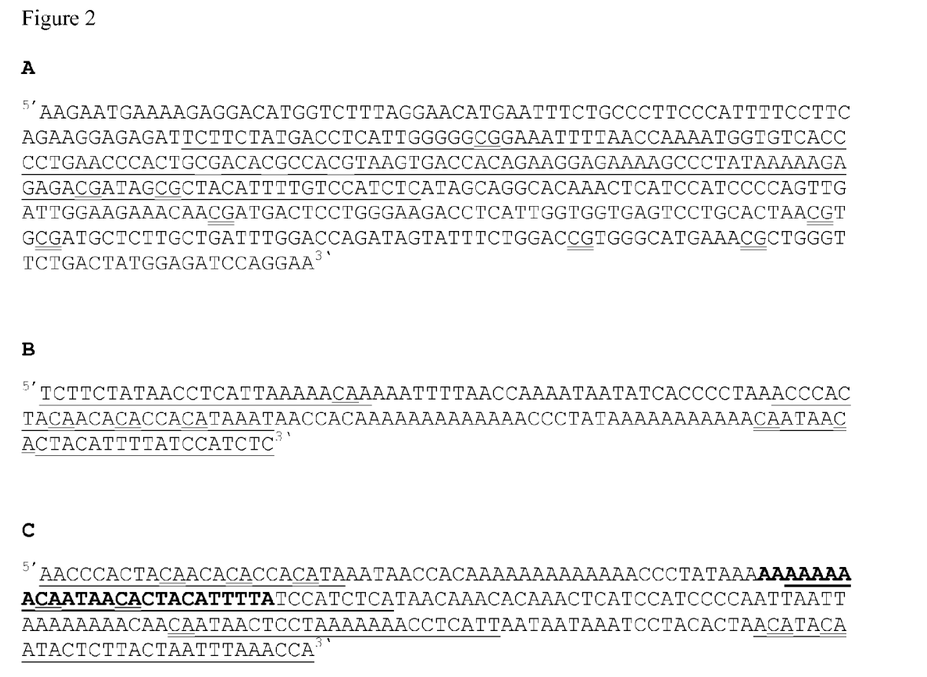
FIG. 2 shows A) the genomic sequence of the amplicon No. 1909 according to SEQ ID No. 1. The target-region of the qPCR-assay is underlined, CpG positions of interest are double underlined; B) the bisulfite-converted target-region 1 of the qPCR-assay-system (TpG-specific), primer and probe are underlined, CpG positions of interest are double underlined; and C) the bisulfite-converted alternative target-region 2 of the qPCR-assay-system (TpG-specific), primer and probe are underlined, the target-region is indicated in bold; CpG positions of interest are double underlined.

SEQ ID NO: 1 shows the nucleotide sequence of AMP 1909;

SEQ ID NO: 2 and SEQ ID NO: 3 show the nucleotide sequence of the target regions according to FIG. 2;

SEQ ID NOs: 4 to 16 show the nucleotide sequences of the primers and probes as used in the examples.

SEQ ID NO: 17 discloses the mRNA for human IL17(A).

SEQ ID NOs: 18 to 22 show the nucleotide sequences of particularly preferred primers and probes as used in example 3.

EXAMPLES

Example 1

The inventors have purified various blood subsets including T cells. DNA from the purified cells was bisulfite-treated analyzed at various CpG dinucleotide motifs. The inventors then compared the methylation status (finding C as for Cytosine that was methylated in the original (genomic) sequence versus T for cytosine that was unmethylated in the original sequence).

Surprisingly, it was found that specific areas in the genomic region of IL-17 was significantly demethylated in IL-17 positive T cells compared to any other cell type.

Then, upon finding of the differential methylation, the inventors analyzed larger genomic regions by means of bisulfite sequencing. This latter procedure served for exploring and extending the differentially methylated region and was conducted, for example with the differentially methylated gene region of IL-17A as disclosed herein.

The strict association of IL-17 positive T cells with the demethylation in the gene and in particular the regions as analyzed (amplicons) could also be surprisingly demonstrated outside of sub-fractions of CD4 positive cells, and was found to be robust also in complex biological samples like whole blood samples or tissue samples (even non-trypsinized).

Example 2

Development of Specific qPCR Assays.

From the results as obtained in Example 1, a genomic region of interest including preferable CpG positions to be analyzed was identified (amplicon 1909, see FIG. 2).

In this region, a detailed analysis was performed in order to develop a highly specific qPCR assay based on the following amplification primers and probe (see FIG. 2B):

```
Forward Primer: qPCR14 nmF2.2:
                                    (SEQ ID NO: 4)
TCTTCTATAACCTCATTAAAAACAA;

Reverse Primer: qPCR14 nmR2.1:
                                    (SEQ ID NO: 5)
GAGATGGATAAAATGTAGTGTTATT;

Hydrolysis Probe: qPCR14 nmP2.3:
                                    (SEQ ID NO: 6)
ACCCACTACAACACACCACATAAAT.
```

Figure 1:
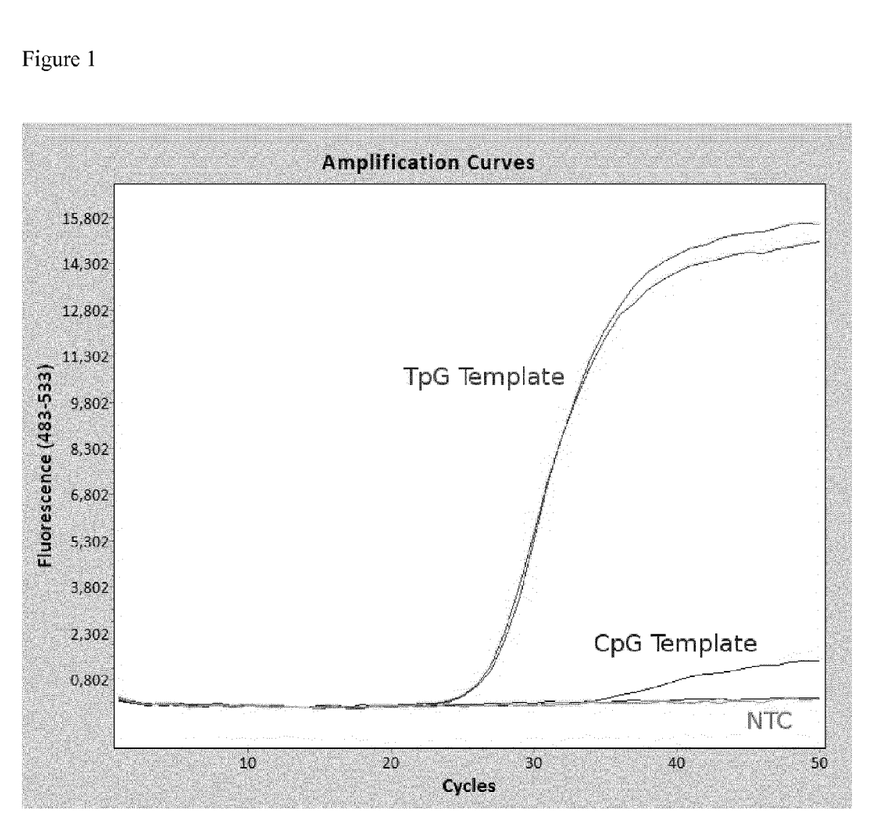
FIG. 1 shows the results of the test-template as amplified according to Example 1. TpG Template: unmethylated test-DNA; CpG template: methylated test-DNA; NTC: No template control.

The specificity of the TpG-specific PCR-system was tested based on test-templates (see FIG. 1) and was found to be highly robust and specific for IL17-positive T cells.

Furthermore, for an alternative assay in the above target-region (region-1) of the qPCR-assay-system primer-variants (alternatives) were developed as follows:

correspond 100% to the original bisulfite treated sequence but include specific mismatches that surprisingly increased the specificity.

| qPCR14 (Th17) Assay | | Run-ID: 110930UB qPCR14 MDA-Dil + WBLs | | | | | | | | |
|---|---|---|---|---|---|---|---|---|---|---|
| Standards for Quantification | | PCR-System specific to "TpG" | | | PCR-System specific to "GAPDH" | | | | | |
| Standard-ID | Plasmid units | CP Value | Plasmid Copies | C.V (%) | CP Value | Plasmid Copies | C.V (%) | Data Analysis | | |
| Standard-1 | 50.000 Copies | 22.9 | 49833.33 | 1.0 | 23.4 | 50933.33 | 6.1 | | | |
| Standard-2 | 10.000 Copies | 25.2 | 10200.00 | 0.98 | 25.7 | 10233.33 | 2.03 | | | |
| Standard-3 | 2.000 Copies | 27.7 | 1943.33 | 1.8 | 28.0 | 2110.00 | 3.3 | | | |
| Standard-4 | 400 Copies | 30.0 | 411.0 | 3.0 | 30.6 | 354.0 | 3.4 | | | |
| Standard-5 | 80 Copies | 32.2 | 78.60 | 12.41 | 32.6 | 86.27 | 3.25 | | | |
| Standard-6 | 16 Copies | 34.20 | 16.10 | ND | 35.19 | 16.00 | 6.19 | 50.16 | 6.24 | 6.19 |
| NTC | No Template Control | ND | ND | ND | ND | ND | ND | | | |
| Analyzed Samples | | PCR-System specific to "TpG" | | | PCR-System specific to "GAPDH" | | | | | |
| Epionts-ID | Customer-ID | CP Value | Plasmid Copies | C.V (%) | CP Value | Plasmid Copies | C.V (%) | Th17 [%] | S.D. | C.V. (%) |
| WBL63 | | 34.17 | 16.70 | 16.86 | 26.07 | 7996.67 | 0.63 | 0.21 | 0.03 | 14.61 |

```
                                              (SEQ ID NO: 7)
qPCR14 nmF2.1: TTCTTCTATAACCTCATTAAAAACA.
and (SEQ ID NO: 8)
qPCR14 nmR2.2: ATGGATAAAATGTAGTGTTATTGT.
```

In addition to the target region (region 1) a further alternative region (region 2) for a qPCR-assay was analyzed within the amplicon No. 1909 using primers and probes as follows (see FIG. 2c):

Amplification primers:

```
                                              (SEQ ID NO: 9)
qPCR14 nmF2.3: AACCCACTACAACACACCACA;

(SEQ ID NO: 10)
qPCR14 nmF2.4: ACCCACTACAACACACCACATA;

(SEQ ID NO: 11)
qPCR14 nmR2.3: AATGAGGTTTTTTAGGAGTTATT;

(SEQ ID NO: 12)
qPCR14 nmR2.4: TGAGGTTTTTTAGGAGTTATTG;

(SEQ ID NO: 13)
qPCR14 nmR2.5. TGGTTTAAATTAGTAAGAGTATTGTAT;

(SEQ ID NO: 14)
qPCR14 nmR2.6: GTTTAAATTAGTAAGAGTATTGTATGT;
```

Hydrolyzation probes for this region would be:

```
                                              (SEQ ID NO: 15)
qPCR14 nmP2.5: AAAAAACAATAACACTACATTTTATCCATCTCA;
and (SEQ ID NO: 16)
qPCR14 nmP2.6: TGAGATGGATAAAATGTAGTGTTATTGTTTTT.
```

Example 3

Development of Optimized Specific IL17A-qPCR Assays.

In order to develop particularly preferred "perfect" primer systems for the assay, primers were developed that do not Table 1 summarizes the results of the qPCR-analysis of the blood sample (WBL63). Shown are the CP-values for the plasmid standards as measured in the LightCycler LC480 and the ones for the blood sample (WBL63), each for the IL17A PCR-system and the GAPDH PCR (control/normalization/standardization) system. Based on the plasmid standard the corresponding copy numbers (plasmid copies) were calculated from the CP-value as measured. Here, the C.V.-value describes the extent of the deviation of the triplicate measurements.

The percent of IL17-positive T-cells in the sample can be calculated from the number of demethylated IL17A-copies (=16.7) and the overall copy number in the sample (=7996.67; measured by the GAPDH-PCR-system) as follows:

% IL17-positive $T$-cells=demethylated IL17$A$-copies/overall copies×100%

IL17-positive $T$-cells=16.7/7996.67×100=0.21%.

Figure 3:
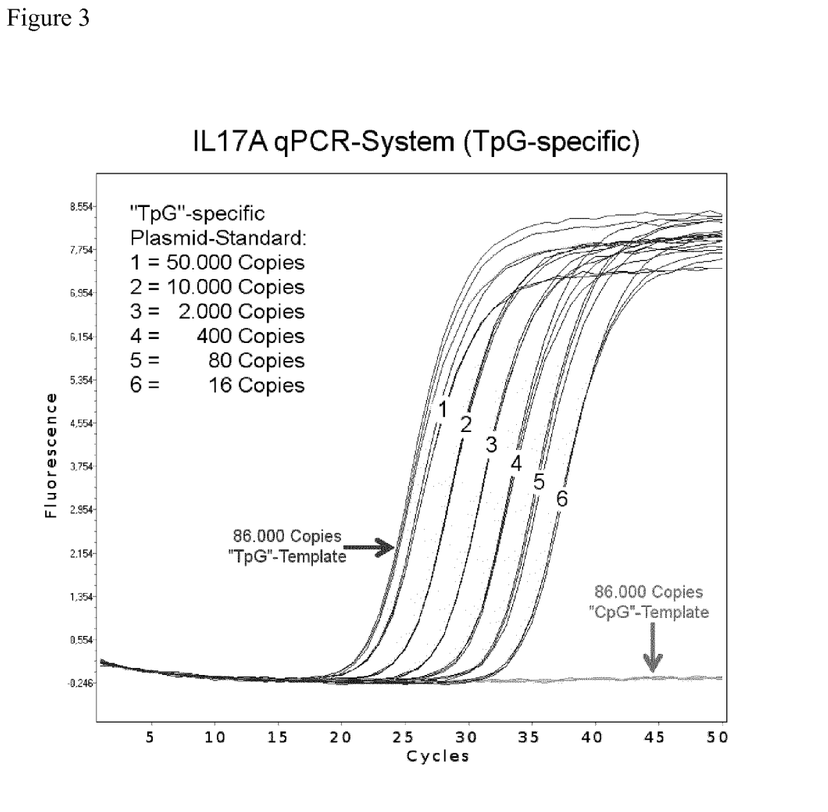
FIG. 3 demonstrates the specificity of the preferred TpG-specific IL17A qPCR-assay system according to Example 3 for demethylated template-DNA. Shown are the amplification profiles of serial dilutions of plasmid standards carrying the target region of the IL17A-gene (bisulfite-converted, unmethylated). In addition, the amplification profiles of unmethylated (TpG; gray curve) and methylated (CpG; dark gray curve) plasmid templates (86000 copies each) are shown. The TpG-specific IL17A qPCR-system amplifies only non-methylated template-DNA with high specificity, but no methylated template, and shows that there is no cross-reactivity from the technical point of view on the assay.
Figure 4:
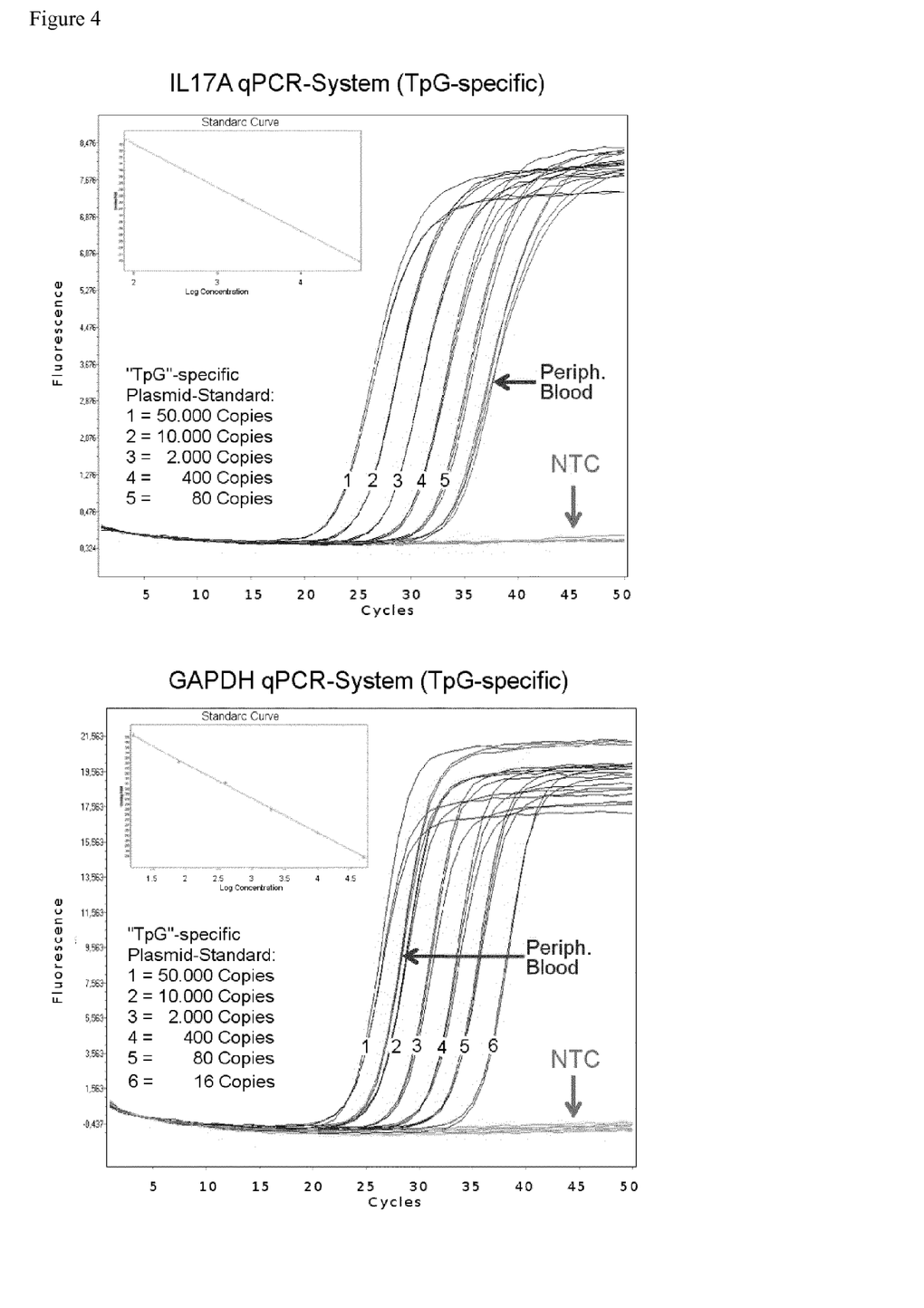
FIG. 4 demonstrates the analysis of a complex sample (e.g. blood sample) (peripheral blood) for a detection of the relative amount of IL17-positive T-cells.

The present assay is special in the sense that the amplification of the demethylated (and bisulfite-converted) IL17A-target-DNA using "common" fitted primers and standard PCR-protocols does not provide a sufficient result. Only after using amplification primers that have a mutation (a "mismatch") at strategic sites as identified herein, together with the use of a much higher $MgCl_2$-concentration in the PCR allows for the efficient amplification of the IL17A-target region. Four particularly preferred primer pairs were thus identified that allowed for a particularly effective amplification of the IL17A-target region, namely PM-2.47 nm, PM-2.48 nm, PM-2.53 nm, and PM-2.54 nm. One primer combination (primer-mix PM-2.53 nm) was particularly effective in the amplification—and thus leads to an improved performance of the qPCR-assay. This primer combination was also used in the experiments shown in FIGS. 3 and 4.

The sequences of the amplification primers and the "Taqman-probe" are as follows. qPCR-Assay—oligonucleotides (5'->3')

1. Amplification Primers

```
Forward Primer qPCR14 nmF2.1_M1:
                                (SEQ ID NO: 18)
ATTCTTCTATAACCTCATTAAAAGCA;

Forward Primer qPCR14 nmF2.2_M1:
                                (SEQ ID NO: 19)
TTCTTCTATAACCTCATTAAAAGCAA;

Reverse Primer qPCR14 nmR2.1:
                                (SEQ ID NO: 20)
GAGATGGATAAAATGTAGTGTTATT;

Reverse Primer qPCR14 nmR2.2b:
                                (SEQ ID NO: 21)
GATGGATAAAATGTAGTGTTATTG.
```

Mismatches in the primer sequence are underlined and bold. For an effective amplification the following primer combinations are used:
PM-2.47 nm: qPCR14 nmF2.1_M1+qPCR14 nmR2.1
PM-2.48 nm: qPCR14 nmF2.1_M1+qPCR14 nmR2.2b
PM-2.53 nm*: qPCR14 nmF2.2_M1+qPCR14 nmR2.1
PM-2.54 nm: qPCR14 nmF2.2_M1+qPCR14 nmR2.2b
* indicates the best amplification efficiency in the test (particularly preferred embodiment).

2. Taqman-Probe

```
                                (SEQ ID NO: 22)
qPCR14 nmP5: CCACTACAACACACCACATAAAT
```

As modified reaction conditions (see above), preferably up to 6.4 mM MgCl$_2$ could be used in the assay, i.e. above 5 mM MgCl$_2$.

Example 4

Proportion of IL17A Positive Cells Measured by Flow Cytometry and Bisulfite Conversion Assay.

The inventors analyzed bisulfite conversion in PMA and ionomycin stimulated and unstimulated peripheral blood samples and monitored demethylation of the IL17A gene. Results were compared to flow cytometry analyses detecting IL17A positive cells (table 2).

|  | % of IL17A demethylated cells assessed via bisulfite conversion | Detection of IL17A producing cells via flow cytometry |
|---|---|---|
| Unstimulated | 1-2% | <0.1% |
| Stimulated e.g. by PMA and ionomycin | 1-2% | 1-2% |

Table 2 summarizes results of flow cytometry and demethylation analysis of IL17A of stimulated and unstimulated peripheral blood.

Results show approx. 1-2% IL17A demethylation in peripheral blood samples of healthy donors which is virtually IL17A negative when tested by flow cytometry. Moreover, after stimulation of peripheral blood with PMA/ionomycin the inventors still measure approx. of 1-2% IL17A demethylation but IL17A protein levels jump up to values of ca. 1-2%.

Surprisingly, the novel assay detects the proportion of IL17A demethylated cells (in %) in a sample—a population that probably resembles the pool of Th17 cells independent from stimulation processes: on the epigenetic scale the novel technology quantifies both, stimulated and un-stimulated Th17 cells, whereas flow cytometry only detects stimulated (i.e., IL17 producing) Th17 cells.

The invention claimed is:

1. A kit comprising:
   a) a bisulfite reagent, and
   b) a combination of: a forward primer, a reverse primer, and a probe, the combination selected from:
      i) the forward primer comprising SEQ ID NO: 4 or 7, the reverse primer comprising SEQ ID NO. 5 or 8 and the probe comprising SEQ ID NO. 6,
      ii) the forward primer comprising SEQ ID NO: 9 or 10, the reverse primer comprising SEQ ID NO: 11, 12, 13, or 14, and the probe comprising SEQ ID NO: 15 or 16, and
      iii) the forward primer comprising SEQ ID NO: 18 or 19, the reverse primer comprising SEQ ID NO: 20 or 21, and the probe comprising SEQ ID NO: 22.

2. The kit of claim 1, wherein the kit comprises the forward primer comprising SEQ ID NO: 4, the reverse primer comprising SEQ ID NO: 5, and the probe comprising SEQ ID NO: 6.

3. The kit of claim 1, wherein the kit comprises the forward primer comprising SEQ ID NO: 4, the reverse primer comprising SEQ ID NO: 8, and the probe comprising SEQ ID NO: 6.

4. The kit of claim 1, wherein the kit comprises the forward primer comprising SEQ ID NO: 7, the reverse primer comprising SEQ ID NO: 5, and the probe comprising SEQ ID NO: 6.

5. The kit of claim 1, wherein the kit comprises the forward primer comprising SEQ ID NO: 7, the reverse primer comprising SEQ ID NO: 8, and the probe comprising SEQ ID NO: 6.

6. The kit of claim 1, wherein the kit comprises the forward primer comprising SEQ ID NO: 9, the reverse primer comprising SEQ ID NO: 11, and the probe comprising SEQ ID NO: 15 or 16.

7. The kit of claim 1, wherein the kit comprises the forward primer comprising SEQ ID NO: 9, the reverse primer comprising SEQ ID NO: 12, and the probe comprising SEQ ID NO: 15 or 16.

8. The kit of claim 1, wherein the kit comprises the forward primer comprising SEQ ID NO: 9, the reverse primer comprising SEQ ID NO: 13, and the probe comprising SEQ ID NO: 15 or 16.

9. The kit of claim 1, wherein the kit comprises the forward primer comprising SEQ ID NO: 9, the reverse primer comprising SEQ ID NO: 14, and the probe comprising SEQ ID NO: 15 or 16.

10. The kit of claim 1, wherein the kit comprises the forward primer comprising SEQ ID NO: 10, the reverse primer comprising SEQ ID NO: 11, and the probe comprising SEQ ID NO: 15 or 16.

11. The kit of claim 1, wherein the kit comprises the forward primer comprising SEQ ID NO: 10, the reverse primer comprising SEQ ID NO: 12, and the probe comprising SEQ ID NO: 15 or 16.

12. The kit of claim 1, wherein the kit comprises the forward primer comprising SEQ ID NO: 10, the reverse primer comprising SEQ ID NO: 13, and the probe comprising SEQ ID NO: 15 or 16.

13. The kit of claim 1, wherein the kit comprises the forward primer comprising SEQ ID NO: 10, the reverse primer comprising SEQ ID NO: 14, and the probe comprising SEQ ID NO: 15 or 16.

14. The kit of claim 1, wherein the kit comprises the forward primer comprising SEQ ID NO: 18, the reverse primer comprising SEQ ID NO: 20, and the probe comprising SEQ ID NO: 22.

15. The kit of claim 1, wherein the kit comprises the forward primer comprising SEQ ID NO: 18, the reverse primer comprising SEQ ID NO: 21, and the probe comprising SEQ ID NO: 22.

16. The kit of claim 1, wherein the kit comprises the forward primer comprising SEQ ID NO: 19, the reverse primer comprising SEQ ID NO: 20, and the probe comprising SEQ ID NO: 22.

17. The kit of claim 1, wherein the kit comprises the forward primer comprising SEQ ID NO: 19, the reverse primer comprising SEQ ID NO: 21, and the probe comprising SEQ ID NO: 22.

* * * * *

```
SEQUENCE LISTING

<160> NUMBER OF SEQ ID NOS: 22

<210> SEQ ID NO 1
<211> LENGTH: 393
<212> TYPE: DNA
<213> ORGANISM: Homo sapiens

<400> SEQUENCE: 1
aagaatgaaa agaggacatg gtctttagga acatgaattt ctgcccttcc cattttcctt      60
cagaaggaga gattcttcta tgacctcatt gggggcggaa attttaacca aaatggtgtc     120
acccctgaac ccactgcgac acgccacgta agtgaccaca gaaggagaaa agccctataa     180
aaagagagac gatagcgcta cattttgtcc atctcatagc aggcacaaac tcatccatcc     240
ccagttgatt ggaagaaaca acgatgactc ctgggaagac ctcattggtg gtgagtcctg     300
cactaacgtg cgatgctctt gctgatttgg accagatagt atttctggac cgtgggcatg     360
aaacgctggg ttctgactat ggagatccag gaa                                 393

<210> SEQ ID NO 2
<211> LENGTH: 142
<212> TYPE: DNA
<213> ORGANISM: Homo sapiens

<400> SEQUENCE: 2
tcttctataa cctcattaaa acaaaaatt ttaaccaaaa taatatcacc cctaaaccca       60
```

```
ctacaacaca ccacataaat aaccacaaaa aaaaaaaaac cctataaaaa aaaaaacaat    120
aacactacat tttatccatc tc                                            142

<210> SEQ ID NO 3
<211> LENGTH: 207
<212> TYPE: DNA
<213> ORGANISM: Homo sapiens

<400> SEQUENCE: 3
aacccactac aacacaccac ataaataacc acaaaaaaaa aaaaccccta taaaaaaaa     60 aacaataaca ctacatttta tccatctcat aacaaacaca aactcatcca tccccaatta   120
attaaaaaaa acaacaataa ctcctaaaaa aacctcatta ataataaatc ctacactaac   180
atacaatact cttactaatt taaacca                                       207

<210> SEQ ID NO 4
<211> LENGTH: 25
<212> TYPE: DNA
<213> ORGANISM: Homo sapiens

<400> SEQUENCE: 4
tcttctataa cctcattaaa aacaa                                          25

<210> SEQ ID NO 5
<211> LENGTH: 25
<212> TYPE: DNA
<213> ORGANISM: Homo sapiens

<400> SEQUENCE: 5
gagatggata aaatgtagtg ttatt                                          25

<210> SEQ ID NO 6
<211> LENGTH: 25
<212> TYPE: DNA
<213> ORGANISM: Homo sapiens

<400> SEQUENCE: 6
acccactaca acacaccaca taaat                                          25

<210> SEQ ID NO 7
<211> LENGTH: 25
<212> TYPE: DNA
<213> ORGANISM: Homo sapiens

<400> SEQUENCE: 7
ttcttctata acctcattaa aaaca                                          25

<210> SEQ ID NO 8
<211> LENGTH: 24
<212> TYPE: DNA
<213> ORGANISM: Homo sapiens

<400> SEQUENCE: 8
atggataaaa tgtagtgtta ttgt                                           24

<210> SEQ ID NO 9
<211> LENGTH: 21
<212> TYPE: DNA
<213> ORGANISM: Homo sapiens

<400> SEQUENCE: 9
aacccactac aacacaccac a                                              21
```

<210> SEQ ID NO 10
<211> LENGTH: 22
<212> TYPE: DNA
<213> ORGANISM: Homo sapiens

<400> SEQUENCE: 10
acccactaca acacaccaca ta                                        22

<210> SEQ ID NO 11
<211> LENGTH: 24
<212> TYPE: DNA
<213> ORGANISM: Homo sapiens

<400> SEQUENCE: 11
aatgaggttt ttttaggagt tatt                                      24

<210> SEQ ID NO 12
<211> LENGTH: 23
<212> TYPE: DNA
<213> ORGANISM: Homo sapiens

<400> SEQUENCE: 12
tgaggttttt ttaggagtta ttg                                       23

<210> SEQ ID NO 13
<211> LENGTH: 27
<212> TYPE: DNA
<213> ORGANISM: Homo sapiens

<400> SEQUENCE: 13
tggtttaaat tagtaagagt attgtat                                   27

<210> SEQ ID NO 14
<211> LENGTH: 27
<212> TYPE: DNA
<213> ORGANISM: Homo sapiens

<400> SEQUENCE: 14
gtttaaatta gtaagagtat tgtatgt                                   27

<210> SEQ ID NO 15
<211> LENGTH: 33
<212> TYPE: DNA
<213> ORGANISM: Homo sapiens

<400> SEQUENCE: 15
aaaaaacaat aacactacat tttatccatc tca                            33

<210> SEQ ID NO 16
<211> LENGTH: 33
<212> TYPE: DNA
<213> ORGANISM: Homo sapiens

<400> SEQUENCE: 16
tgagatggat aaaatgtagt gttattgttt ttt                            33

<210> SEQ ID NO 17
<211> LENGTH: 1859
<212> TYPE: DNA
<213> ORGANISM: Homo sapiens

<400> SEQUENCE: 17

```
gcaggcacaa actcatccat ccccagttga ttggaagaaa caacgatgac tcctgggaag      60
acctcattgg tgtcactgct actgctgctg agcctggagg ccatagtgaa ggcaggaatc     120
acaatcccac gaaatccagg atgcccaaat tctgaggaca agaacttccc ccggactgtg     180
atggtcaacc tgaacatcca taaccggaat accaatacca atcccaaaag gtcctcagat     240
tactacaacc gatccaccte accttggaat ctccaccgca atgaggaccc tgagagatat     300
ccctctgtga tctgggaggc aaagtgccgc cacttgggct gcatcaacgc tgatgggaac     360
gtggactacc acatgaactc tgtccccatc cagcaagaga tcctggtcct gcgcagggag     420
cctccacact gccccaactc cttccggctg gagaagatac tggtgtccgt gggctgcacc     480
tgtgtcaccc cgattgtcca ccatgtggcc taagagctct ggggagccca cactccccaa     540
agcagttaga ctatggagag ccgacccagc ccctcaggaa ccctcatcct tcaaagacag     600
cctcatttcg gactaaactc attagagttc ttaaggcagt ttgtccaatt aaagcttcag     660
aggtaacact tggccaagat atgagatctg aattaccttt ccctctttcc aagaaggaag     720
gtttgactga gtaccaattt gcttcttgtt tactttttta agggctttaa gttatttatg     780
tatttaatat gccctgagat aactttgggg tataagattc cattttaatg aattacctac     840
tttattttgt ttgtcttttt aaagaagata agattctggg cttgggaatt ttattattta     900
aaaggtaaaa cctgtatttt tttgagctat ttaaggatct atttatgttt aagtatttag     960
aaaaaggtga aaaagcacta ttatcagttc tgcctaggta aatgtaagat agaattaaat    1020
ggcagtgcaa aatttctgag tctttacaac atacggatat agtatttcct cctctttgtt    1080
tttaaaagtt ataacatggc tgaaaagaaa gattaaacct actttcatat gtattaattt    1140
aaattttgca atttgttgag gttttacaag agatacagca agtctaactc tctgttccat    1200
taaaccctta taataaaatc cttctgtaat aataaagttt caaagaaaaa tgtttatttg    1260
ttctcattaa atgtatttta gcaaactcag ctcttcccta ttgggaagag ttatgcaaat    1320
tctcctataa gcaaaacaaa gcatgtcttt gagtaacaat gacctggaaa tacccaaaat    1380
tccaagttct cgatttcaca tgccttcaag actgaacacc gactaaggtt ttcatactat    1440
tagccaatgc tgtagacaga agcattttga taggaataga gcaaataaga taatggccct    1500
gaggaatggc atgtcattat taaagatcat atggggaaaa tgaaaccctc cccaaaatac    1560
aagaagttct gggaggagac attgtcttca gactacaatg tccagtttct ccccctagact   1620 caggcttcct ttggagatta aggcccctca gagatcaaca gaccaacatt tttctcttcc    1680
tcaagcaaca ctcctagggc ctggcttctg tctgatcaag gcaccacaca acccagaaag    1740
gagctgatgg ggcagaacga actttaagta tgagaaaagt tcagcccaag taaaataaaa    1800
actcaatcac attcaattcc agagtagttt caagtttcac atcgtaacca ttttcgccc     1859
```

<210> SEQ ID NO 18
<211> LENGTH: 26
<212> TYPE: DNA
<213> ORGANISM: Homo sapiens

<400> SEQUENCE: 18
attcttctat aacctcatta aaagca                                            26

<210> SEQ ID NO 19
<211> LENGTH: 26
<212> TYPE: DNA
<213> ORGANISM: Homo sapiens

<400> SEQUENCE: 19

```
ttcttctata acctcattaa aagcaa                                              26

<210> SEQ ID NO 20
<211> LENGTH: 25
<212> TYPE: DNA
<213> ORGANISM: Homo sapiens

<400> SEQUENCE: 20
gagatggata aaatgtagtg ttatt                                               25

<210> SEQ ID NO 21
<211> LENGTH: 24
<212> TYPE: DNA
<213> ORGANISM: Homo sapiens

<400> SEQUENCE: 21
gatggataaa atgtagtgtt attg                                                24

<210> SEQ ID NO 22
<211> LENGTH: 23
<212> TYPE: DNA
<213> ORGANISM: Homo sapiens

<400> SEQUENCE: 22
ccactacaac acaccacata aat                                                 23
```